United States Patent [19]

Campolmi et al.

[11] 4,239,914

[45] Dec. 16, 1980

[54] PROCESS FOR PREPARING 2-(6'-METHOXY-2'-NAPHTHYL)-PROPIONIC ACID

[75] Inventors: Stefano Campolmi; Maria G. Felicioli, both of Novara; Vittorio Carletti, Meda; Roberto Santi, Novara, all of Italy

[73] Assignee: Montedison S.p.A., Milan, Italy

[21] Appl. No.: 40,955

[22] Filed: May 21, 1979

[30] Foreign Application Priority Data

May 22, 1978 [IT] Italy .............................. 23652 A/78

[51] Int. Cl.$^3$ ....................... C07C 65/00; C07C 65/11
[52] U.S. Cl. ................................................. 562/466
[58] Field of Search ....................................... 562/466

[56] References Cited

U.S. PATENT DOCUMENTS 3,637,767  1/1972  Alvarez .

FOREIGN PATENT DOCUMENTS 1274271  5/1972  United Kingdom .

OTHER PUBLICATIONS

Compere, G. L. Jr., JOC 33 (6) Jun. 1969, pp. 2565-2566.
Merz, A. Synthesis, Oct. 1974, p. 729.
Merz, A. et al., Chem. Ber. 110, 96–106 (1977).
Chem. Abst. 86, 1977, 29502b.
Fiorini, M. et al., Journal of Molecular Catalysis, 4(1978), 125134.

*Primary Examiner*—Paul J. Killos

[57] ABSTRACT

There is disclosed an improved process for selectively preparing 2-(6'-methoxy-2'-naphthyl)-propionic acid in the active antipode (+) form by reacting 2-acetyl-6-methoxynaphthalene, in an organic solvent, with a system consisting of (a) a haloform selected from $CHCl_3$ and $CHBr_3$;
(b) an aqueous solution of an inorganic base selected from NaOH and KOH; and
(c) a crown-ether or hydrocarbyl salt of quaternary ammonium, or of phosphonium;

and hydrogenating the 2-(6'-methoxy-2'-naphthyl)-acrylic acid thus formed to obtain 2-(6'-methoxy-2'-naphthyl)-propionic acid.

29 Claims, No Drawings

PROCESS FOR PREPARING 2-(6'-METHOXY-2'-NAPHTHYL)-PROPIONIC ACID

THE PRIOR ART

Processes for preparing naphthyl-propionic acids in general are known, as are pharmaceutical preparations in the form of solutions, suspensions, pills, capsules, etc., useful as anti-inflammation agents, analgesics, antipyretic and antipruitic agents, etc., and comprising said acids.

One known process for preparing 2-(6'-methoxy-2'-naphthyl)-propionic acid involves starting with 2-acetyl-6-methoxynaphthalene, epoxydizing it and then obtaining the corresponding aldehyde. The 2-(6'-methoxy-2'-naphthyl)-propionic acid in its turn is obtained from the resulting aldehyde by oxidation thereof or from the aldehyde by hydrolysis of the cyanhydrin, hydrogenation, etc. In that process, the 2-(6'-methoxy-2'-naphthyl)-propionic acid is obtained in racemic form, from which the optic antipode (+) can be separated by means of conventional separating media, such as treatment of the racemate with activated bases, etc.

Said known process requires a large number of operations and, furthermore, the selectivity for the active antipode (+) is not high.

THE PRESENT INVENTION

An object of this invention is to provide an improved process for preparing 2-(6'-methoxy-2'-naphthyl)-propionic acid which is simpler and therefore more economical than the known processes and in which the active antipode (+) form of the acid is produced selectively.

That and other objects are achieved by the present invention in accordance with which 2-(6'-methoxy-2'-naphthyl)-propionic acid of the formula

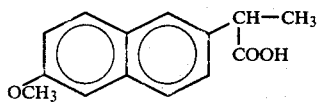

is produced with a high degree of selectivity of the optical antipode (+) form by reacting 2-acetyl-6-methoxynaphthalene of the formula:

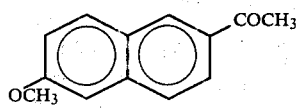

in an organic solvent, with a system consisting of
(a) a haloform which is $CHCl_3$ or $CHBr_3$;
(b) an aqueous solution of an inorganic base which is NaOH or KOH; and
(c) a crown-ether or hydrocarbyl salt of quaternary ammonium, or of phosphonium,
at a temperature of from 0° C. to about 50° C., and hydrogenating the resulting 2-(6'-methoxy-2'-naphthyl)-acrylic acid of the formula:

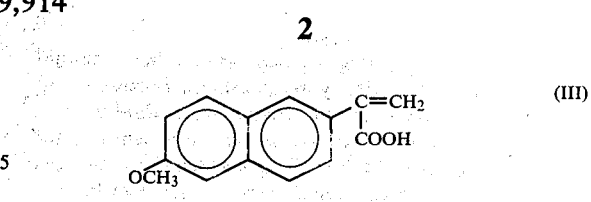

to obtain the acid of formula (I).

In one aspect of the present invention, the asymmetric hydrogenation of 2-(6'-methoxy-2'-naphthyl)-acrylic acid (III) is conducted in the homogeneous phase in the presence of particular catalysts based on complexed rhodium which will be particularly defined hereinafter.

The reaction is schematically represented by the following equations (1) and (2):

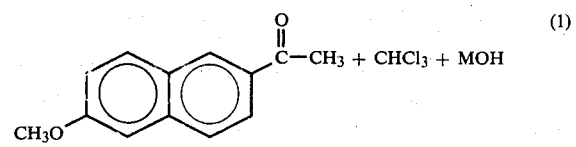

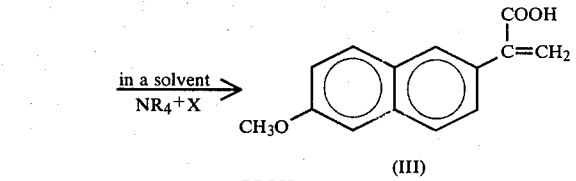

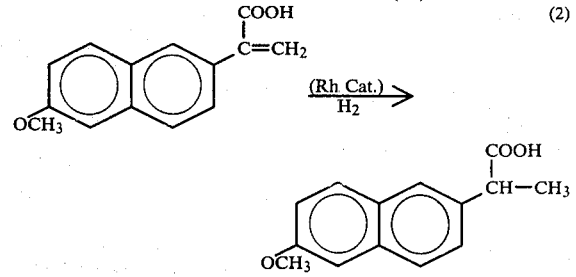

in which M is Na or K and $NR_4^+$ X, with X being Cl, Br or OH, is the quaternary ammonium salt, which may be, also, a phosphonium salt or a crown-ether, as more fully defined hereinafter.

More concisely, the process of this invention consists in reacting compound (II), 2-acetyl-6-methoxynaphthalene, with the diphase system made up, as explained hereinbefore, of an organic phase containing compound (II) and chloroform or bromoform, and of an aqueous phase containing KOH or NaOH in the presence of salts of alkyl- and/or aryl-ammonium or phosphonium or of the crown-ethers, acid (III) i.e., 2-(6'-methoxy-2'-naphthyl)-acrylic acid being obtained.

This behaviour of compound (II) is all the more surprising since those skilled in the art had to reasonably expect that, under our conditions, the acid obtained would be 2-hydroxy-(6'-methoxy-2'-naphthyl)-propionic acid (X):

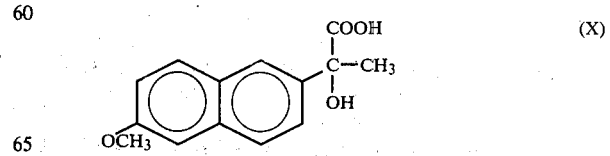

With respect to the general prior art, the present invention represents, therefore, a surprising departure from a prejudice inherent in said prior art. According to the art, (saturated) hydroxy-arylacetic acids covered by formula (X) can be prepared by reaction of aldehydes or ketones with alkaline hydrates and bromoform or chloroform, wherefore this teaching in itself would have dissuaded the technician skilled in the art from further researches on said reaction in order to obtain the unsaturated compound (III), which is, surprisingly, obtained in the process of the present invention.

In fact, reaction (1), conducted under our conditions, leads, selectively, to a substantial and prevailing obtainment of compound (III) with only lesser amounts of compound (X).

2-acetyl-6-methoxynaphthalene (II) is a known compound obtainedable, for example, from 6-methoxynaphthalene, which is acetylated with acetyl chloride in the presence of aluminum chloride in a nitrobenzenic medium.

The reaction resulting in acid (III) is conducted in an organic solvent, with a molar ratio of the solvent to acetyl-derivative (II) ranging from 10:1 to 100:1.

The aliphatic, aromatic hydrocarbons and the halogen-derivatives thereof, the ethers, the alkyl ethers of (poly)ethylene glycols, pyridines, picolines, quinolines have proved to be efficient solvents.

As stated previously, the haloform is selected from $CHCl_3$ and $CHBr_3$. Preferably, it is $CHCl_3$ in a molar ratio to acetyl-derivative (II) comprised between about 1:1 and about 1:3.

The inorganic base, used in aqueous solution, is selected from NaOH and KOH. Preferably, it is KOH, having a concentration ranging from 15% to 50% by weight, according to a molar ratio to acetyl-derivative (II) higher than 4:1.

The quaternary salt, as defined herein, is selected from those of ammonium and/or phosphonium of hydrocarbyls containing up to 20 carbon atoms. The quaternary salt may be replaced by crown-ethers.

Suitable quaternary ammonium salts include benzyl-trimethylammonium chloride, tetrabutylammonium chloride and iodide, di-hexadecyl-diethylammonium chloride, benzyl-triethylammonium chloride and benzyl-trimethylammonium hydroxide.

The crown-ethers employed are cyclic polyethers known in the literature as complexing agents for alkaline metals (J. of Am. Chem. Soc. 89:26, Dec. 20, 1967, 7017-7036) and available on the market.

Crown-ethers include dicyclohexyl-18-crown-6- and dibenzo-18-crown-6. As already indicated hereinabove, in order to conduct the reaction it is possible to utilize the corresponding salts of "onium" (sulphonium, phosphonium) having, as is known to those skilled in the art, the nature of functional equivalence, for the purposes of the reaction with the quaternary ammonium salts.

The temperature preferably ranges from 0° C. to 50° C.; reaction times of about 24 to 60 hours are sufficient to allow the completion of the reaction, depending on the parameters of temperature, concentration, etc.

The quaternary ammonium salt or the crown-ether is added in a catalytic amount, according to the usual technique followed for phase transfer reactions.

The 2-(6'-methoxy-2'-naphthyl)-acrylic acid (III) so obtained is then hydrogenated to the 2-(6'-methoxy-2'-naphthyl)propionic acid (I).

Hydrogenation may be conducted in a conventional manner, e.g., with catalysts of palladium on carbon, or rhodium on carbon, etc. In this way, acid (I) is obtained in racemic form, from which form (+) can be separated by using known techniques, for example, by means of optically active alkaloid bases such as cinchonidine, etc.

Alternatively, according to a presently preferred embodiment of the invention, and as already indicated, hydrogenation can be conducted stereoselectively to the desired optical form (+) by using asymmetric hydrogenation catalysts in a homogeneous phase.

The 2-(6'-methoxy-2'-naphthyl)-acrylic acid (III) is thus stereoselectively hydrogenated in a homogeneous system consisting of: (a) Rhodium-based catalysts complexed with phosphines, (b) an organic solvent and, optionally (c) in the presence of a nitrogeneous base of formula $N(R)_3$ more closely defined later on, with $H_2$.

The rhodium complexes used are neutral or cationic complexes known in the literature and they are thus chosen from among those having formulae (IV) and (V):

$$[Rh\ Chel\ (L-L)]^+X^- \qquad (IV)$$

and

$$[Rh\ Chel\ (L-L)\ Y] \qquad (V)$$

wherein:

Chel represents a phosphinic bidented chiral compound with a chelating action;

L—L represents a molecule of a diolefin or two molecules of a monoolefin;

$X^-$ represents an anion chosen from among $PF_6^-$, $BF_4^-$, $ClO_4^-$, $B(C_6H_5)_4^-$;

Y represents a halogen, chosen from among Cl, Br and I.

The phosphinic bidented chiralic compound (Chel) with a chelating action is a phosphine or an aminophosphine, asymmetric with respect to the carbon or phosphorus atom, chosen from among those having formulae (VI), (VII) and (VIII):

$$R^*N-(PPh_2)-CH_2-CH_2(PPh_2)NR^*; \qquad (VI)$$

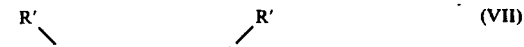

(VII)

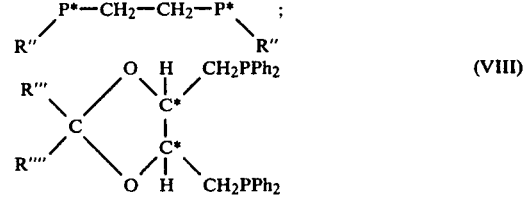

(VIII)

wherein:

R* is chosen from between (+)alpha-methylbenzyl and (+)menthyl;

R' and R", always different from each other, are chosen among the alkyls, cycloalkyls and aryls having up to 10 carbon atoms, also substituted in their turn;

R''' and R'''' represent indifferently alkyls having up to 3 carbon atoms.

In the formulae (VI), (VII), and (VIII) the asterisks * indicate the asymmetry center of the molecule. Preferred chiralic compounds are: [2,3,0-isopropylidene-2,3-dihydroxy-1,4-bis(diphenylphosphine)butane], (−DIOP); N, N'-bis-((+)alphamethylbenzyl), N, N'-bis-(diphenylphosphine) ethylenediamine, (phenethyl-PNNP), and 1,2-ethanediylbis(o-methoxyphenyl)-phenylphosphine.

The above indicated phosphines and aminophosphines are known compounds that may be prepared according to conventional methods.

For instance, there may be used a chelating phosphine of formula (IX) of the type (VIII):

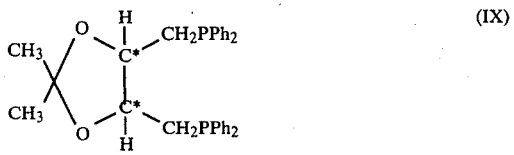

Said phosphine, (—)DIOP, [2,3,0-isopropylidene-2,3-dihydroxy-1,4-bis(diphenylphosphine)butane] may be prepared from a chiralic compound easily available, that is the 1(+)-tartaric acid.

The olefin (L—L), as hereinabove defined, is chosen from among both the conjugated as well as the unconjugated, linear or cyclic diolefins, and from amongst linear and cyclic olefins.

Effective results have been achieved by the use of 1,3-cyclooctadiene(COD), norbornadiene, cyclooctene(COT), 1,5-hexadiene, ethylene, etc.

The organic solvent that keeps the hydrogenation system homogeneous is chosen from among the lower alkyl alcohols, having up to 4 carbon atoms with a linear or branched chain, and preferably is methanol or ethanol.

As said above, the hydrogenation reaction is conducted optionally in the presence of nitrogenous bases, $NH_3$ or amines.

Thus, said compound is chosen from between ammonia and mono-, di- and tri-substituted aliphatic amines of formula $N(R)_3$ wherein R is chosen from between H and/or alkyls having up to 10 carbon atoms.

Preferred amines are: triethylamine, tributylamine, or $NH_3$ is used.

The operating conditions, otherwise substantially conventional, foresee temperatures comprised between about 0° and 70° C.; pressures of gaseous $H_2$ comprised between 1 and about 50 ata. and hydrogenation times comprised between about 1 and 100 hours.

The catalyst/substrate (I) molar ratio may vary between about 1:20 and about 1:300.

The substrate (I)/nitrogenous base molar ratio is comprised between 1:1 and about 30:1.

The substrate (I)/solvent ratio may vary from 1:100 to about 1:10 by weight.

The optical activity is measured in chloroform, at a concentration of about 1 gram per 100 cc of solution and compared with the $[\alpha]_D^{25}$ given in the literature as +65.5 (C=in $CHCl_3$).

Hydrogenation can be carried out either directly on the optionally dehydrated reaction mixture containing the unsaturated acid (III), or after separation of the acid (III) by means of conventional techniques, for example by fraction crystallization, etc.

According to one effective embodiment, the process of the invention is carried out as follows:

The alkaline aqueous solution at the desired concentration, and the quaternary ammonium salt, are introduced into a thermoregulated reactor, equipped with a stirrer, a thermometer and a system for feeding the reagents. Successively, at about 0° C., the solvent, the haloform and acetyl-derivative (II) are charged into the reactor, and the whole is brought to room temperature under continuous vigorous stirring. The reaction is continued for the desired stretch of time, keeping the system under stirring.

At the conclusion of the reaction, the mixture is poured into water at 10% $H_2SO_4$, whereupon it is extracted with ether. The ether solution is treated with aqueous 10% $Na_2CO_3$, acidified, extracted, etc., according to conventional techniques.

The acid (III) thus obtained is then hydrogenated according to the known conventional techniques with catalysts such as for instance Pd on carbon etc., or by using the stereoselective method in accordance with this invention.

The solution is prepared separately in the chosen solvent preliminarily degassed, containing the substrate (III) to be hydrogenated, the catalyst and, possibly the amine. This solution is then transferred, in the absence of oxygen, into an autoclave provided with a vigorous stirrer, and in which it is maintained under a hydrogen atmosphere at the desired temperature, pressure and time.

At the end of the hydrogenation, the acid (I) is separated according to conventional methods. The process, thanks to the mild operating conditions and the high selectivity for the desired product (I), turns out to be particularly convenient.

This process will now be described in more detail by means of the following examples that are given, however, for merely illustrative and not limiting purposes.

The symbols used have the meanings already indicated herein previously.

EXAMPLE 1

4.2 g of KOH (0.075 mole), 4.2 g of $H_2O$ (0,018 mole), and 0.45 g of benzyl-triethylammonium chloride (0,002 mole) were introduced into a 50 cc flask equipped with a stirer. After cooling to 0° C., 2 g of 6-methoxy-2-acetylnaphthalene (0.01 mole), 1.2 g of chloroform (0.01 mole) in 20 cc of toluene were added. The mass was intensely stirred at such temperature for 6 hours, then at room temperature for 60 hours.

At the conclusion of the reaction, the mixture was poured into water and 10% sulphuric acid and it was extracted with ether. The ethereal extract was treated with a 10% aqueous solution of $Na_2CO_3$. The aqueous phase was acidified and extracted with ether. It was dried with anhydrous sodium sulphate and by evaporation it was possible to obtain 0.65 g of raw acid, consisting for 75% of 2-(6'-methoxy-2'-naphthyl)-acrylic acid and for 25% of the corresponding hydroxyacid.

From the ethereal solution of the first extraction, 1.4 of unreacted 6-methoxy-2-acetylnaphthalene were recovered. The resulting acid mixture was introduced into a 25 cc flask equipped with a stirrer, along with 7.6 cc of dimethyl ether of triethylene glycol (triglime) and 0.06 cc of concentrated sulphuric acid, and the whole was heated for about 2 minutes to 150° C. After cooling by dilution with water in excess, a solid precipitated, which was filtered and washed. 0.5 g of 2-(6'-methoxy-2'-naphthyl)-acrylic acid (0.0022 mole) were obtained, which could be further purified by crystallization from chloroform.

The unsaturated acid thus obtained is introduced into a 100 cc reactor fitted with a stirrer, and into which are then introduced under a nitrogen atmosphere:

0.061 g of $[Rh(COD)(-DIOP)]^+ClO_4^-$; 20 cc of distilled and degassed isopropanol;

30 μl of distilled triethylamine.

This solution is then transferred, by means of a vacuum system, into a 50 cc autoclave made of stainless steel and fitted with a magnetic stirrer, and into which is then fed hydrogen until bringing the pressure up to 3.5 ata.

The temperature is maintained at 25° C. for 17 hours. At the end of the reaction, the reaction product is brought to dryness and then diluted with methylene chloride. The product is then extracted with diluted (2 N) ammonia. The aqueous phase is then brought to a pH=1 with a 20% $H_2SO_4$ and extracted with ether. The ethereal extract is then dried on anhydrous $Na_2SO_4$, thereupon treated with active carbon, filtered and evaporated until obtaining 0.49 g of hydrogenated acid (I). The hydrogenation yield equalled 95%. Optical purity was 33%.

EXAMPLE 2

By operating according to Example 1 and with the same amounts of reagents, but with reaction times of 6 hours at 0° C. and of 12 hours at room temperature, it was possible to obtain 0.4 g of raw acid consisting for 80% of 2-(6'-methoxy-2'-naphthyl)-acrylic acid and for the remaining 20% of the corresponding oxyacid.

By fractional crystallization from chloroform, 0.25 g (0.0011 mole) of 2-(6'-methoxy-2'-naphthyl)-acrylic acid were obtained, which, by hydrogenation according to the modalities of Example 1, provided 0.24 g of product having an optical purity of 33%.

EXAMPLE 3

4.2 g of KOH, 4.2 g of $H_2O$ and 0.45 g of benzyltriethylammonium chloride were introduced into a 50 cc flask and cooled to 0° C., after which 2 g of 6-methoxy-2-acetylnaphthalene and 2.5 g of bromoform in 20 cc of benzene were introduced. The whole was maintained at 0° C. for 6 hours and at room temperature for a further 18 hours. The mixture was then treated according to the modalities of Example 1, so as to obtain 0.7 g of raw acid which contained 0.25 g of 2-(6'-methoxy-2'-naphthyl)-acrylic acid and 0.25 g of the corresponding oxyacid. The resulting acid mixture was dehydrated in dimethyl ether of triethyleneglycol (triglime) with concentrated sulphuric acid according to the modalities of Example 1.

The unsaturated acid so otained was hydrogenated dissolved in 20 cc of ethanol in the presence of 50 mg of carbon-supported palladium. On conclusion of the absorption (about 4 hours), the reaction was stopped, the reaction mass was filtered and evaporated. By crystallization of the residue from acetone-hexane, 0.3 g of 2-(6'-methoxy-2'-naphthyl)-propionic acid in the racemic form were obtained.

EXAMPLE 4

Operating as in Example 3, but using chloroform instead of bromoform for a reaction time of 48 hours, it was possible to obtain 1 g of raw acid in a ratio by weight of 2-(6'-methoxy-2-naphthyl)-acrylic acid to oxyacid equal to 3:1, and which was treated as in Example 3.

EXAMPLE 5

7.5 g of NaOH, 7.5 g of $H_2O$ and 0.23 g of benzyl-triethyl-ammonium chloride were introduced into a 50 cc flask, cooled to 0° C., and 1 g of 6-methoxy-2-acetylnaphthalene and 1.2 cc of chloroform in 10 cc of chlorobenzene were introduced. The whole was maintained at 5°–10° C. for 24 hours. The mixture was then treated according to the same modalities of Example 1, to obtain 0.42 g of rough acid consisting of 2-(6'-methoxy-2'-naphthyl)-acrylic acid and the corresponding oxyacid in a ratio of 3:1. The mixture was then treated as in Example 3.

EXAMPLE 6

By operating according to Example 5, but using tetrahydrofuran instead of chlorobenzene, it was possible to obtain 1.1 g of raw acid containing the acids of Example 5 in a ratio of 2:1.

EXAMPLE 7

By repeating Example 5, but using dimethoxyethane instead of chlorobenzene, it was possible to obtain 1.07 g of raw acid with a ratio of the acid components equal to 2:1. The mixture was then treated as in Example 3.

EXAMPLE 8

Operating as in Example 1, and using 20 cc of $CH_3OH$ instead of isopropanol, for a reaction time of 22 hours, there were obtained a hydrogenation yield of 100% and an optical purity of 72%.

EXAMPLE 9

Operating as in Example 1 and using 20 cc of absolute ethanol instead of isopropanol, for a reaction time of 20 hours, there were obtained a hydrogenation yield of 100% and an optical purity equal to 72%.

EXAMPLE 10

Operating as in Example 9, and using as a catalyst 0.072 g of [Rh(COT)$_2$(−DIOP)Cl], for a reaction time of 19 hours, there were obtained a hydrogenation yield of 71% and an optical purity of 62.7%.

EXAMPLE 11

Operating according to Example 9, with a hydrogen pressure of 1 ata. for a reaction time of 96 hours, there were obtained a hydrogenation yield of 84% and an optical purity of 49%.

EXAMPLE 12

Operating as in Example 8, at a temperature of 50° C. and for a reaction time of 3 hours, there were obtained a hydrogenation yield of 100% and an optical purity of 51%.

EXAMPLE 13

Into a 100 cc reactor were fed under a nitrogen atmosphere:
0.15 g of [Rh(+)phenethyl-PNNP(COD)]$^+$ClO$_4^-$;
0.5 g of unsaturated acid (III);
20 cc of degassed anhydrous ethanol.

The system was then connected with a burette containing $H_2$ and maintained under stirring in this $H_2$ atmosphere, at a temperature of about 20° C. for 18 hours.

The hydrogenated product was thereupon separated by means of the method described in Example 1; thereby were obtained 0.4 g of saturated acid (I).

The hydrogenation yield amounted to 71% while the optical purity was equal to 4.2%.

EXAMPLE 14

Operating as in Example 8, but in the absence of triethylamine, for a reaction time of 5 hours, there were obtained a hydrogenation yield of 100% and an optical purity of 18%.

The 2-(6'-methoxy-2'-naphthyl)-propionic acid obtained by the present process has the same pharmaceutical uses as the acid produced by the known methods.

What we claim is:

1. Process for preparing (2-(6'-methoxy-2'-naphthyl)-propionic acid of the formula:

$$\text{(I)} \quad \underset{OCH_3}{\text{naphthalene}}-\underset{COOH}{\overset{CH-CH_3}{|}}$$

characterized in that 2-acetyl-6-methoxynaphthalene having the formula:

$$\text{(II)} \quad \underset{OCH_3}{\text{naphthalene}}-COCH_3$$

is reacted in organic solvents with a system consisting of:
(a) a haloform selected from $CHCl_3$ and $CHBr_3$,
(b) an aqueous solution of an inorganic base selected from NaOH and KOH, and
(c) a compound selected from the crown-ethers and the hydrocarbyl salts of quaternary ammonium and phosphonium, at a temperature comprised between approximately 0° and 50° C., and in that from the resulting 2-(6'-methoxy-2'-naphthyl)-acrylic acid of formula:

$$\text{(III)} \quad \underset{OCH_3}{\text{naphthalene}}-\underset{COOH}{\overset{C=CH_2}{|}}$$

acid (I) is obtained by hydrogenation in the presence of a catalyst selected from rhodium and palladium catalysts.

2. The process of claim 1 in which the catalyst is selected from rhodium on carbon and palladium on carbon.

3. The process of claim 1, in which the organic solvent is selected from the aliphatic and aromatic hydrocarbons, the halogen-derivatives thereof, ethers, alkyl ethers of (poly)ethylene glycols, pyridines, picolines and quinolines.

4. The process of claim 3, in which the solvent is selected from toluene, benzene, chlorobenzene, tetrahydrofuran, dimethoxyethane.

5. The process of claim 1, in which the organic solvent is employed in a molar ratio to 2-acetyl-6-methoxynaphthalene (II) ranging from 10:1 to 100:1.

6. The process of claim 1, in which the haloform is used in a molar ratio to 2-acetyl-6-methoxynaphthalene (II) ranging from about 1:1 to about 1:3.

7. The process of claim 6, in which the haloform is chloroform.

8. The process of claim 1, in which the inorganic base aqueous solution is at a concentration, by weight, ranging from about 15% to about 50%.

9. The process of claim 8, in which the inorganic base is KOH.

10. The process of claim 1, in which the molar ratio of NaOH or KOH to 2-acetyl-6-methoxynaphthalene (II) is higher than 4:1.

11. The process of claim 1, in which the quaternary salt is selected from the ammonium and phosphonium salts of hydrocarbyls having up to 20 carbon atoms.

12. The process of claim 1, in which the quaternary ammonium salt is selected from benzyl-trimethylammonium chloride, tetrabutylammonium chloride and iodide, di-hexadecyldiethylammonium chloride, benzyl-triethylammonium chloride, benzyl-trimethylammonium hydroxide.

13. The process of claim 12, in which the quaternary ammonium salt is benzyl-triethylammonium chloride.

14. The process of claim 1, in which the crown-ether is selected from dicyclohexyl-18-crown-6 and dibenzo-18-crown-6.

15. Process according to claim 1, characterized in that the hydrogenation of 2-(6'-methoxy-2'-naphthyl)-acrylic acid (III) is conducted in a homogeneous system consisting of: (a) a Rhodium catalyst complexed with phosphines, (b) an organic solvent and optionally (c) a nitrogenous base.

16. Process according to claim 15, characterized in that the phosphinic Rhodium complex is selected from those having formulae (IV) and (V):

$$[\text{Rh Chel (L—L)}]^+ X^- \quad \text{(IV)}$$

and $$[\text{Rh Chel (L—L) Y}] \quad \text{(V)}$$

wherein:
Chel represents a chiral bidented phosphinic compound with a chelating action;
L—L represents one molecule of a diolefine or two molecules of a monoolefine;
$X^-$ represents an anion chosen from amongst $PF_6^-$, $BF_4^-$, $ClO_4^-$, $B(C_6H_5)_4^-$;
Y represents a halogen chosen from amongst Cl, Br and J.

17. Process according to claim 15, characterized in that the chiral bidented phosphinic compound with a chelating action is a phosphine or an amino-phosphine selected from those of formulae (VI), (VII) and (VIII):

$$R^*N-(PPh_2)-CH_2-CH_2(PPh_2)NR^*; \quad \text{(VI)}$$

$$\underset{R''}{\overset{R'}{\diagdown}}P^*-CH_2-CH_2P^*\underset{R''}{\overset{R'}{\diagup}} \quad \text{(VII)}$$

(VIII) [diagram of chelate structure with $R'''$, $R''''$, O, H, $C^*$, $CH_2PPh_2$ groups]

wherein:
$R^*$ is chosen from between (+)alpha-methylbenzyl and (+)menthyl;
$R'$ and $R''$, always different from each other, are selected from alkyls, cycloalkyls and aryls having up to 10 carbon atoms, also substituted;
$R'''$ and $R''''$ represent indifferently alkyls having up to 3 carbon atoms.

18. Process according to claim 17, characterized in that the chiral bidented phosphinic compound is selected from: [2,3,0-isopropylidene-2,3-dihydroxy-1,4-bis(diphenylphosphine)butane]; N,N'-bis(+)alphamethylbenzyl, N,N'-bis(diphenylphosphine)ethylendiamine and 1,2 ethanediyl-bis(o-methoxyphenyl)-phenylphosphine.

19. Process according to claim 15, characterized in that the organic solvent is an alkyl alcohol having up to 4 carbon atoms.

20. Process according to claim 15, characterized in that the reaction is conducted in the presence of a nitrogenous base of formula $N(R)_3$ in which R represents indifferently a hydrogen atom or an alkyl having up to 10 carbon atoms.

21. Process according to claim 15 and following, characterized in that said process is conducted at temperatures comprised between about 0° C. and 70° C.

22. Process according to claim 15 and following, characterized in that said process is conducted at gaseous hydrogen pressure comprised between 1 ata. and about 50 ata.

23. Process according to claim 15 and following, characterized in that the molar ratio phosphinic complex of the Rhodium catalyst/substrate (III) is comprised between 1:20 and 1:300 about.

24. Process according to claim 15 and following, characterized in that the molar ratio substrate (III)/nitrogenous base is comprised between 1:1 and about 1:30.

25. Process according to claim 15 and following, characterized in that the ratio substrate (III)/solvent is comprised between 1:100 and about 1:10 by weight.

26. Process according to claim 15 and following characterized in that the hydrogenation of the 2-(6'-methoxy-2'-naphthyl)acrylic acid (III) is conducted in a homogeneous phase in the presence of Rhodium complex catalysts having the formulae:

[Rh(COD)(−)DIOP]+ClO$_4$; [Rh(COT)$_2$(−)DIOP Cl] and [Rh(+)phenetyl-PNNP(COD)]+ClO$_4^-$ wherein (−)DIOP is 2,3,0-isopropylidene-2,3-dihydroxy-1,4-bis-(diphenylphosphine)butane; COD is the cyclooctadiene, COT the cyclooctene and phenetyl-PNNP stands for N,N'-bis((+)alphamethylbenzyl), N,N'-bis(diphenylphosphine)ethylenediamine.

27. The process of claim 1, in which the hydrogenation of 2-(6'-methoxy-2'-naphthyl)-acrylic acid (III) is effected in the presence of a complexed Rhodium catalyst in the reaction medium of 2-acetyl-6-methoxynaphthalene (II).

28. The process of claim 15, in which the alkyl alcohol is selected from methanol and ethanol.

29. The process of claim 15, in which the nitrogenous base is selected from ammonia, triethylamine and tributylamine.

* * * * *